United States Patent
Wu et al.

(10) Patent No.: US 11,732,042 B2
(45) Date of Patent: Aug. 22, 2023

(54) COMPOSITIONS AND METHODS FOR USING THE CD2-BASED SIGNALING PATHWAYS TO BLOCK HIV INFECTION

(71) Applicants: Yuntao Wu, Manassas, VA (US); Hong Shang, Shenyang (CN)

(72) Inventors: Yuntao Wu, Manassas, VA (US); Hong Shang, Shenyang (CN)

( * ) Notice: Subject to any disclaimer, the term of this patent is extended or adjusted under 35 U.S.C. 154(b) by 428 days.

(21) Appl. No.: 16/755,176

(22) PCT Filed: Oct. 10, 2018

(86) PCT No.: PCT/US2018/055298
§ 371 (c)(1),
(2) Date: Apr. 10, 2020

(87) PCT Pub. No.: WO2019/075125
PCT Pub. Date: Apr. 18, 2019

(65) Prior Publication Data
US 2021/0179712 A1 Jun. 17, 2021

Related U.S. Application Data

(60) Provisional application No. 62/570,947, filed on Oct. 11, 2017.

(51) Int. Cl.
*A61P 31/18* (2006.01)
*C07K 16/28* (2006.01)
*A61K 47/68* (2017.01)
*A61K 38/17* (2006.01)

(52) U.S. Cl.
CPC ...... *C07K 16/2806* (2013.01); *A61K 38/1709* (2013.01); *A61K 47/6811* (2017.08); *A61P 31/18* (2018.01); *C07K 2317/24* (2013.01); *C07K 2317/75* (2013.01); *C07K 2319/30* (2013.01)

(58) Field of Classification Search
CPC ............ C07K 16/2806; C07K 2317/24; C07K 2317/75; C07K 2319/30; A61K 38/1709; A61K 47/6811; A61K 2039/505; A61P 31/18; C12N 2501/51; C12N 2501/53; C12N 5/0638

USPC .................................................. 424/133.1
See application file for complete search history.

(56) References Cited

U.S. PATENT DOCUMENTS

| | | | |
|---|---|---|---|
| 5,795,572 | A | 8/1998 | Diegel et al. |
| 2001/0023072 | A1 | 9/2001 | Crawford et al. |
| 2006/0099177 | A1 | 5/2006 | June et al. |
| 2006/0204500 | A1 | 9/2006 | June et al. |
| 2008/0071063 | A1* | 3/2008 | Allan ............... A61P 29/00 530/387.1 |

FOREIGN PATENT DOCUMENTS

EP 0626447 A1 * 11/1994 ............. C12N 15/13

OTHER PUBLICATIONS

International Search Report & Written Opinion for PCT/US18/55298, dated Feb. 4, 2019.
Sijia He et al., "Prestimulation of CD2 confers resistance to HIV-1 latent infection in blood resting CD4 T cells," Science, Nov. 19, 2021, vol. 24.
Sijia He et al., "Supplemental information: Prestimulation of CD2 confers resistance to HIV-1 latent infection in blood resting CD4 T cells," iScience, Nov. 19, 2021, vol. 24.
P Bressler et al., "Anti-CD2 receptor antibodies activate the HIV long terminal repeat in T lymphocytes," J Immunol, Oct. 1, 1991, pp. 2,290-2,294, vol. 147, No. 7. (abstract only).
Ulrike Erben et al., "Targeting human CD2 by the monoclonal antibody CB.219 reduces intestinal inflammation in a humanized transfer colitis model," Clinical Immunology, Jan. 2015, pp. 16-25, vol. 157.
Office action for related China Application No. 2018800667986, dated Mar. 3, 2023.

* cited by examiner

*Primary Examiner* — Yan Xiao
(74) *Attorney, Agent, or Firm* — Pilloff Passino & Cosenza LLP; Sean A. Passino; Rachel K. Pilloff

(57) ABSTRACT

The present disclosure relates to composition and methodology for using the CD2 receptor to block viral replication, such as HIV-1 infection. In one embodiment, viral target cells such as blood CD4 T cells can be rendered resistant to HIV through stimulation of the CD2 receptor with either an antibody, a ligand, or a small molecule that binds to the CD2 receptor. Pre-stimulation of CD2 can be used to enhance the anti-HIV immunity and used to promote immune response from HIV infection or from an anti-HIV vaccine.

10 Claims, 5 Drawing Sheets

COMPOSITIONS AND METHODS FOR USING THE CD2-BASED SIGNALING PATHWAYS TO BLOCK HIV INFECTION

CROSS REFERENCE

This application claims priority benefit to U.S. Provisional Application No. 62/570,947, filed Oct. 11, 2017, the content of which application is incorporated herein by reference in its entirety.

FIELD

The present disclosure relates to modulating cellular bioactivity, including modulating cellular susceptibility to bacteria and/or viruses, and delivering chemical compounds and ingredients, such as medical drugs, nucleic acids, and proteins, into cells. Provided herein are methodology, compositions, and the like for modulating cellular bioactivity.

INTRODUCTION

CD2 (cluster of differentiation 2, also alternatively called T11/Leu-5, LFA-2, LFA-3 receptor, erythrocyte receptor and rosette receptor) is a co-stimulatory and cell adhesion molecule displayed on the surface of T cells and some NK cells (natural killer cells) but not on B lymphocytes, and thus, is used in immunohistochemistry to identify T cells and NK cells in tissue sections. CD2 is also expressed on all peripheral blood T cells and is one of the earliest T-cell markers on more than 95% of thymocytes. Monoclonal antibodies directed against CD2 inhibit the formation of rosettes with sheep erythrocytes, suggesting that it may be the erythrocyte receptor or is closely associated with it.

CD2 also interacts with other adhesion molecules such as LFA-3/CD58 (lymphocyte function-associated antigen-3). The extracellular domain of CD2 contains immunoglobulin-like domains that can mediate homodimerisation (Chen et al., 2002). Ligation of CD2 by LEA-3 facilitates T cells adhesion to antigen-presenting cells. Similar stimulation of CD2 also initiates signal transduction pathways that modulate cofilin activity and actin cytoskeleton, enhancing T cell activation. However, CD2 knockout mice exhibit essentially normal immune function (Killeen et al., 1992), and it is believed that CD2 is somewhat functionally redundant with other T cell co-stimulatory molecules such as CD28 (Hutchcroft et al., 1998).

SUMMARY

In one aspect, provided is a method for blocking HIV infection in a cell, comprising pre-stimulating the CD2 receptor with an antibody, a ligand, or a small molecule. In one embodiment, the antibody is a an anti-CD2 antibody, selected from UMCD2, BTI-322, CB.219, and Siplizumab. In another embodiment, the ligand is selected from CD58 and Alefacept, and a protein that binds to CD2. In another embodiment, the small molecule is a small molecule that interacts with CD2 and acts as an agonist or antagonist. In another embodiment, the cells are human cells.

In another aspect, provided is a method for treating or preventing HIV infection, comprising administering a composition that pre-stimulates the CD2 receptor. In one embodiment, the composition comprises an antibody, a ligand, or a small molecule. In one embodiment, the antibody is a an anti-CD2 antibody, selected from UMCD2, BTI-322, CB.219, and Siplizumab. In another embodiment, the ligand is selected from CD58 and Alefacept, and a protein that binds to CD2. In another embodiment, the small molecule is a small molecule that interacts with CD2 and acts as an agonist or antagonist.

In another aspect, provided is a composition for treating or preventing HIV infection, wherein said composition pre-stimulates the CD2 receptor. In one embodiment, the composition comprises an antibody, a ligand, or a small molecule.

In another aspect, the disclosure provides methodology for blocking viral nuclear migration in immune cells, comprising pre-stimulating the CD2 receptor with an antibody, a ligand, or a small molecule. In one embodiment, the antibody is a an anti-CD2 antibody, selected from UMCD2, BTI-322, CB.219, and Siplizumab. In another embodiment, the ligand is selected from CD58 and Alefacept, and a protein that binds to CD2. In another embodiment, the small molecule is a small molecule that interacts with CD2 and acts as an agonist or antagonist. In another embodiment, the cells are human cells.

In another aspect, provided is a composition for degrading virion particles in cells, wherein said composition pre-stimulates the CD2 receptor.

In another aspect, the disclosure provides methodology for enhancing anti-HIV immunity, comprising pre-stimulating the CD2 receptor with an antibody, a ligand, or a small molecule. In one embodiment, the antibody is a an anti-CD2 antibody, selected from UMCD2, BTI-322, CB.219, and Siplizumab. In another embodiment, the ligand is selected from CD58 and Alefacept, and a protein that binds to CD2. In another embodiment, the small molecule is a small molecule that interacts with CD2 and acts as an agonist or antagonist.

It is to be understood that both the foregoing general description and the following detailed description are exemplary and explanatory only and are not restrictive of the invention, as claimed.

The accompanying drawings, which are incorporated in and constitute a part of this specification, illustrate several embodiments and together with the description, serve to explain the principles of the invention.

DETAILED DESCRIPTION

Figure 1:
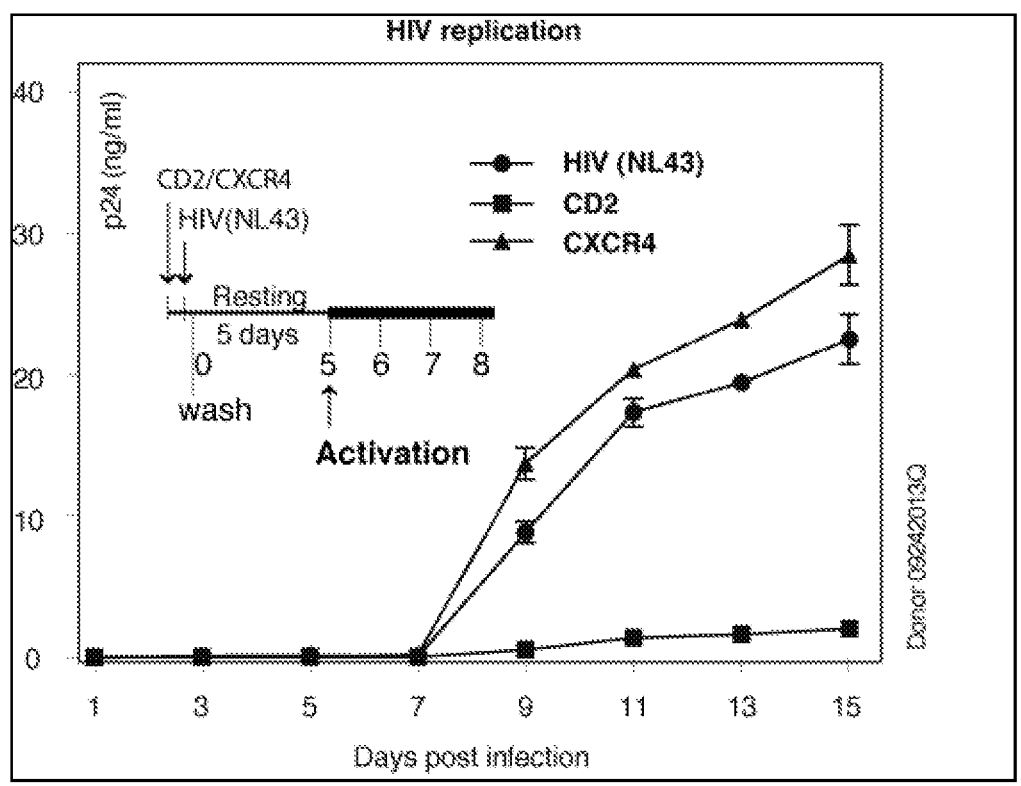
FIG. 1: Pre-stimulation of CD2 inhibits HIV infection of blood CD4 T cells. Resting CD4 T cells were purified by negative depletion from the peripheral blood of healthy donors. Cells were pre-stimulated overnight with anti-CD2 antibody conjugated magnetic beads (2 beads per cell). Following stimulation, cells were infected with HIV-1(NL4-3) for 2 h, washed, and cultured for 5 days, and then activated with anti-CD3/CD28 beads (4 beads per cell).

Reference will now be made in detail to the embodiments and examples of practicing which are illustrated in the accompanying drawings.

The present disclosure relates to compositions and methodology for using the CD2 receptor to block HIV-1 infection. In one embodiment, the present inventors demonstrate that viral target cells such as blood CD4 T cells can be rendered resistant to HIV through stimulation of the CD2 receptor with either an antibody, a ligand, or a small molecule that binds to the CD2 receptor.

The present inventors determined that pre-stimulation of CD2 receptor blocks viral replication in immune cells. Thus, it may be used to treat HIV infection, and it may also promote the degradation of the virion particles in cells, facilitating the antigen presentation process. Pre-stimulation of CD2 can be used to enhance the anti-HIV immunity and used to promote immune response from HIV infection or from an anti-HIV vaccine.

All technical terms in this description are commonly used in biochemistry, molecular biology and immunology, respectively, and can be understood by those skilled in the field of this invention. Those technical terms can be found in: MOLECULAR CLONING: A LABORATORY MANUAL, 3rd ed., vol. 1-3, ed. Sambrook and Russel, Cold Spring Harbor Laboratory Press, Cold Spring Harbor, N.Y., 2001; CURRENT PROTOCOLS IN MOLECULAR BIOLOGY, ed. Ausubel et al., Greene Publishing Associates and Wiley-Interscience, New York, 1988 (with periodic updates); SHORT PROTOCOLS IN MOLECULAR BIOLOGY: A COMPENDIUM OF METHODS FROM CURRENT PROTOCOLS IN MOLECULAR BIOLOGY, 5.sup.th ed., vol. 1-2, ed. Ausubel et al., John Wiley & Sons, Inc., 2002; GENOME ANALYSIS: A LABORATORY MANUAL, vol. 1-2, ed. Green et al., Cold Spring Harbor Laboratory Press, Cold Spring Harbor, N.Y., 1997; CELLULAR AND MOLECULAR IMMUNOLOGY, 4.sup.th ed. Abbas et al., WB Saunders, 1994.

As contemplated herein, a composition can be delivered into the body and onto a cell in any form by any effective route, including but not limited to oral, parenteral, enteral, intraperitoneal, topical, transdermal (e.g., using any standard patch), ophthalmic, nasally, local, non-oral, such as aerosol, spray, inhalation, percutaneous (epidermal), subcutaneous, intravenous, intramuscular, buccal, sublingual, rectal, vaginal, intra-arterial, mucosal, and intrathecal. A composition can be administered alone, or in combination with any ingredient(s), active or inactive.

Any subject can be administered a composition, such as a composition comprising an antibody, ligand, and/or a small molecule, including subjects who have been exposed to HIV, but have not yet developed HIV infection, as well as subjects who have progressed to one or more of the clinical symptoms of HIV infection (e.g., AIDS). In addition to treating and/or preventing HIV infection in humans, such a composition can be used to treat other organisms (e.g., non-human primates, cats, etc.) infected with HIV, or HIV-related viruses, such as SIV, SHIV, or FIV. Thus, subjects who can be treated include, e.g., mammals, humans, monkeys, apes, chimpanzees, gorillas, cats, dogs, mice, rats, etc.

A composition, such as a composition comprising an antibody, ligand, and/or a small molecule can be used to treat and/or prevent infection caused by any HIV virus type, including, but is no limited to, HIV-1 (e.g., clades A, B, C, D, and G, R5 and R5X4 viruses, etc.), HIV-2 (e.g., R5 and R5X4 viruses, etc.), simian immunodeficiency virus (SIV), simian/human immunodeficiency virus (SHIV), feline immunodeficiency virus (FIV), bovine immunodeficiency virus (BIV) (Wright et al., Vet. Res. Commun., 26:239-50, 2002), HTLV-1, HTLV-2, etc.

Pre-stimulation refers to exposing a CD2 receptor to an antibody, ligand, or small molecule before exposing the cell to viral infection, such as any HIV virus.

Post-stimulation means exposing a cell to viral infection and then exposing CD2 on the cell to an antibody, ligand, or small molecule.

Antibody refers to an antibody that pre-stimulates a CD2 receptor, such as for example anti-CD2 antibody. In some embodiments, the anti-CD2 antibody is chosen from -UMCD2 (an anti-human CD2 monoclonal antibody); BTI-322 (BTI-322 is a monoclonal anti-CD2 antibody for treatment of steroid-resistant acute graft-versus-host disease); CB.219 (monoclonal anti-human CD2 antibody); and Siplizumab (monoclonal anti-human CD2 antibody).

Ligand refers to any molecule that binds to the CD2 receptor. An illustrative ligand is CD58. In some embodiments, the ligand is Alefacept (Alefacept is a fusion protein combining the first extracellular domain of LFA3 (CD58) with constant regions ($CH_2$ and $CH_3$) and the hinge domain of human IgG1. This hybrid molecule can be used to bind to CD2 to treat psoriasis vulgaris).

Small molecule refers to small molecules that interact with CD2 and act as an agonist or antagonist.

Illustrative Examples are presented below. They are exemplary and non-limiting.

EXAMPLE 1

Pre-Stimulation of CD2 Inhibits HIV Infection of Blood CD4 T Cells

As exemplified in FIG. 1, pre-stimulation of CD2 inhibits HIV infection of blood CD4 T cells. Resting CD4 T cells were purified by negative depletion from the peripheral blood of healthy donors. Cells were pre-stimulated overnight with anti-CD2 antibody conjugated magnetic beads (2 beads per cell). Following stimulation, cells were infected with HIV-1(NL4-3) for 2 h, washed, and cultured for 5 days, and then activated with anti-CD3/CD28 beads (4 beads per cell).

The CD2-mediated inhibition is not limited to the CXCR4-utilizing viral strains (X4). When we tested an CCR5-utilizing virus (R5), HIV-1(AD8), for the infection of memory CD4 T cells, we observed similar inhibition of HIV-1(AD8). See, e.g., FIG. 2. In addition, when CD4 T cells were pre-stimulated with the CD2 ligand, LFA-3 (CD58), we observed similar inhibition of HIV infection. See, e.g., FIG. 3.

EXAMPLE 2

Pre-Stimulation of CD2 Inhibits R5 HIV Infection of Blood Memory CD4 T Cells

Figure 2:
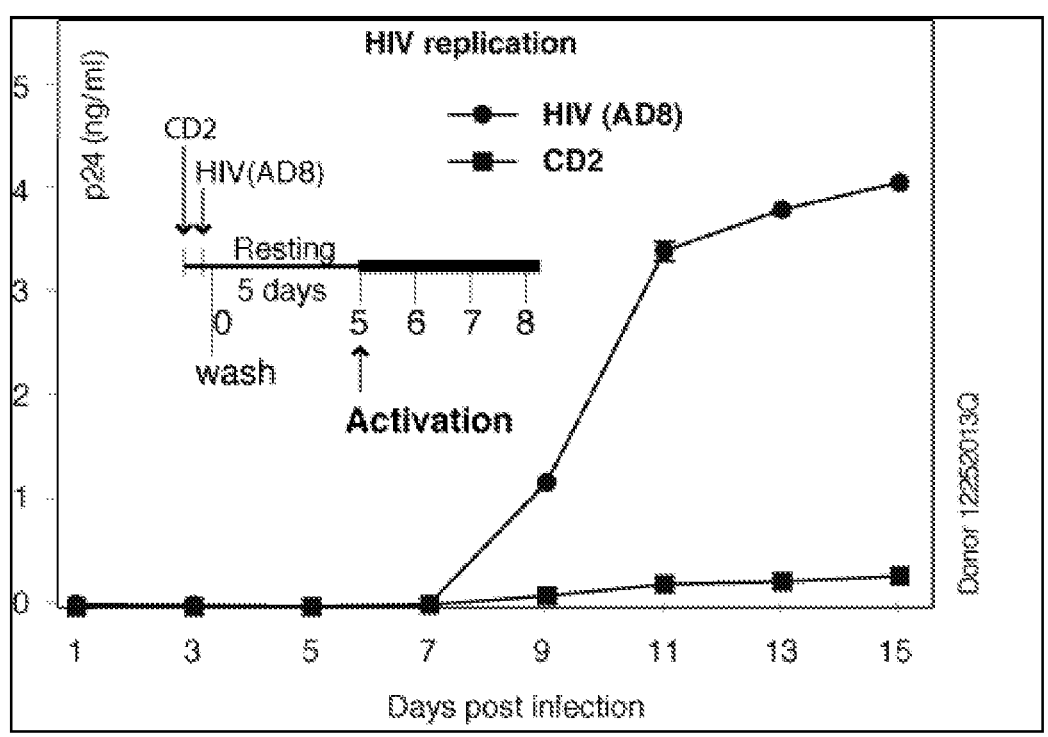
FIG. 2: Pre-stimulation of CD2 inhibits R5 HIV infection of blood memory CD4 T cells. Resting memory CD4 T cells (CD45RO+CD45RA−) were purified by negative depletion from the peripheral blood of healthy donors. Cells were pre-stimulated overnight with anti-CD2 antibody conjugated magnetic beads (2 beads per cell). Following stimulation, cells were infected with HIV-1(AD8) for 2 h, washed, and cultured for 5 days, and then activated with anti-CD3/CD28 beads (4 beads per cell).

As exemplified in FIG. 2, pre-stimulation of CD2 inhibits R5 HIV infection of blood memory CD4 T cells. Resting memory CD4 T cells (CD45RO+CD45RA−) were purified by negative depletion from the peripheral blood of healthy donors. Cells were pre-stimulated overnight with anti-CD2 antibody conjugated magnetic beads (2 beads per cell). Following stimulation, cells were infected with HIV-1(AD8) for 2 h, washed, and cultured for 5 days, and then activated with anti-CD3/CD28 beads (4 beads per cell).

EXAMPLE 3

Pre-Stimulation of CD2 with CD58 Inhibits HIV Infection of Blood CD4 T Cells

Figure 3:
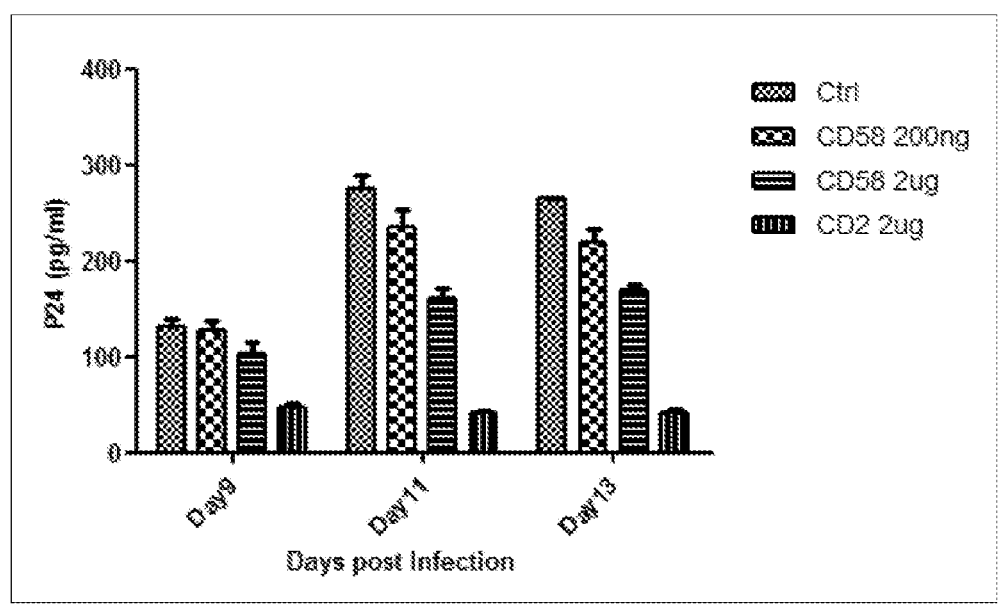
FIG. 3: Pre-stimulation of CD2 with CD58 inhibits HIV infection of blood CD4 T cells. Resting CD4 T cells were purified by negative depletion from the peripheral blood of healthy donors. Cells were pre-stimulated overnight with purified CD58 protein. Following stimulation, cells were infected with HIV for 2 h, washed, and cultured for 5 days, and then activated with anti-CD3/CD28 beads (4 beads per cell).

As shown in FIG. 3, pre-stimulation of CD2 with CD58 inhibits HIV infection of blood CD4 T cells. Resting CD4 T cells were purified by negative depletion from the peripheral blood of healthy donors. Cells were pre-stimulated overnight with purified CD58 protein. Following stimulation, cells were infected with HIV for 2 h, washed, and cultured for 5 days, and then activated with anti-CD3/CD28 beads (4 beads per cell).

Figure 4:
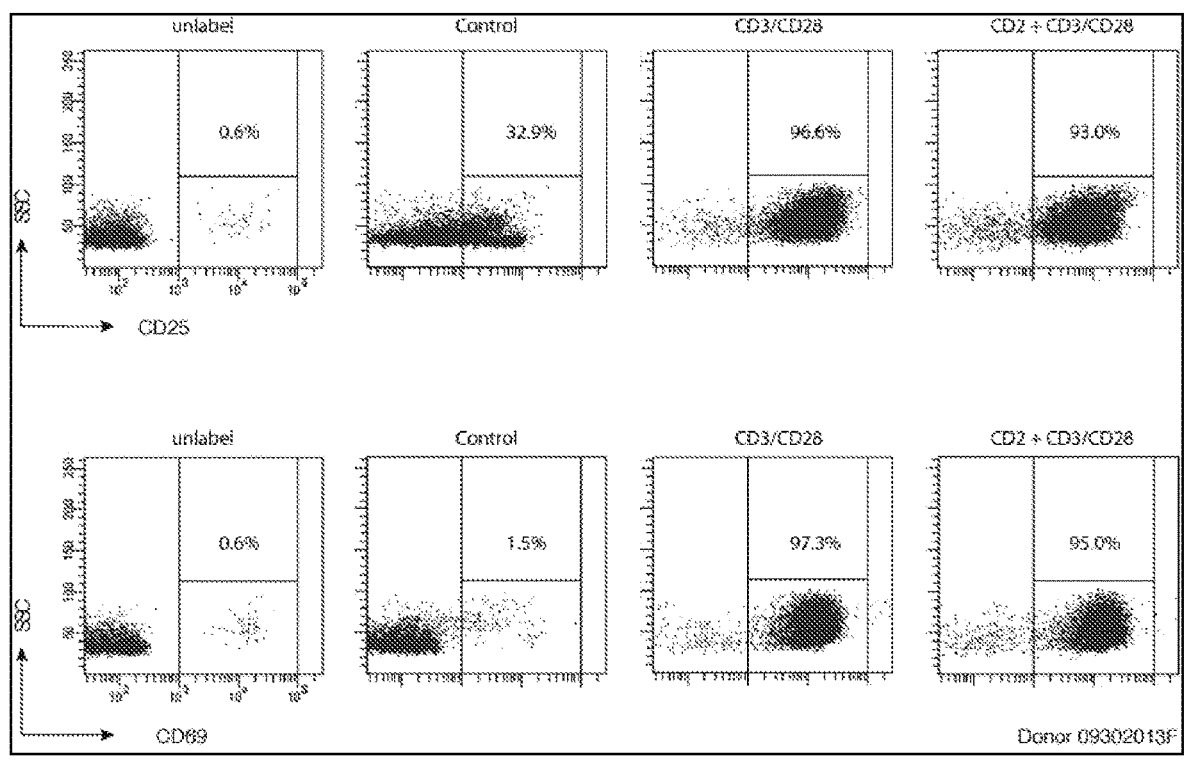
FIG. 4: Pre-stimulation of CD2 does not inhibit T cell activation. Resting CD4 T cells were purified by negative depletion from the peripheral blood of healthy donors. Cells were pre-stimulated overnight with anti-CD2 antibody conjugated magnetic beads (2 beads per cell). Following stimulation, cells were activated with anti-CD3/CD28 beads (4 beads per cell). Up-regulation of CD25 and CD69 was used to measure T cell activation.
Figure 5:
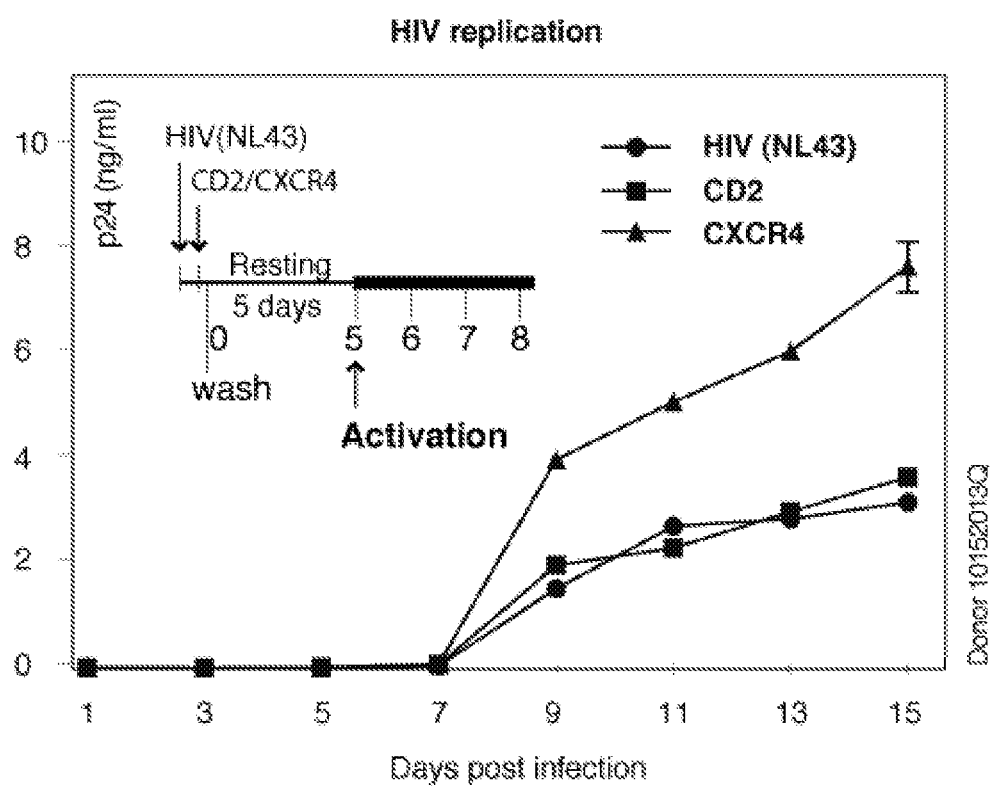
FIG. 5: Post-stimulation of CD2 does not inhibit HIV infection of blood CD4 T cells. Resting CD4 T cells were purified by negative depletion from the peripheral blood of healthy donors. Cells were infected with HIV-1(NL4-3) for 2 h, washed, and then stimulated with anti-CD2 antibody conjugated magnetic beads (2 beads per cell). Following stimulation, cells were cultured for 5 days, and then activated with anti-CD3/CD28 beads (4 beads per cell).

The inhibition of HIV infection by CD2-stimulation did not result from possible inhibition of T cell activation or cytotoxicity. First, and as shown in FIG. 4, when CD2-stimulated resting CD4 T cells were activated with anti-CD3/CD28 magnetic beads, we did not observe a defect in T cell activation. Additionally, and as shown in FIG. 5, if resting CD4 T cells were infected with HIV-1 for 2 hours, and then stimulated with the anti-CD2 antibody, there was no inhibition of HIV-1. These results suggested CD2-stimulation specifically blocked a viral early infection process such as viral nuclear migration. It is likely that CD2 signaling alters the cofilin pathway, inhibition viral nuclear migration. HIV-mediated CXCR4/cofilin activation has been known to be required for viral nuclear migration (Yoder et al., 2008).

EXAMPLE 4

Levels of Cofilin Phosphorylation and Dephosphorylation as a Measure of the Degree of Stimulation One is able to quantify levels of cofilin phosphorylation and dephosphorylation to measure the degree of stimulation. Cofilin is inactivated by phosphorylation at Ser-3 and reactivated by dephosphorylation. Protein phosphorylation can be determined by any method known in the art, including but not limited to radioactive $^{32}$P radioactive labeling, molybdate-based colorimetric determination, phosphor-specific antibodies for use in Western blot or ELISA, phosphor-staining reagents, and various mass spectrometry and flow cytometry methods.

REFERENCES

Chen, H. A., Pfuhl, M., and Driscoll, P. C. (2002). The pH dependence of CD2 domain 1 self-association and 15N chemical exchange broadening is correlated with the anomalous pKa of Glu41. Biochemistry 41, 14680-14688.

Hutchcroft, J. E., Slavik, J. M., Lin, H., Watanabe, T., and Bierer, B. E. (1998). Uncoupling activation-dependent HS1 phosphorylation from nuclear factor of activated T cells transcriptional activation in Jurkat T cells: differential signaling through CD3 and the costimulatory receptors CD2 and CD28. J Immunol 161, 4506-4512.

Killeen, N., Stuart, S. G., and Littman, D. R. (1992). Development and function of T cells in mice with a disrupted CD2 gene. EMBO J 11, 4329-4336.

Yoder, A., Yu, D., Dong, L., Iyer, S. R., Xu, X., Kelly, J., Liu, J., Wang, W., Vorster, P. J., Agulto, L., et al. (2008). HIV envelope-CXCR4 signaling activates cofilin to overcome cortical actin restriction in resting CD4 T cells. Cell 134, 782-792.

Other embodiments will be apparent to those skilled in the art from consideration of the specification and practice of the description herein. It is intended that the specification and examples be considered as exemplary only, with a true scope and spirit of the invention being indicated by the following claims.

What is claimed is:

1. A method for treating or preventing HIV infection in an HIV-uninfected T-cell, comprising administering to said cell, a composition that pre-stimulates the CD2 receptor, wherein said composition comprises an antibody or ligand, wherein the ligand is selected from the group consisting of CD58 and Alefacept.

2. The method of claim 1, wherein said composition comprises the antibody.

3. The method of claim 2, wherein the antibody is an anti-CD2 antibody.

4. The method of claim 3, wherein the anti-CD2 antibody is selected from the group consisting of UMCD2, BTI-322; CB.219, and Siplizumab.

5. The method of claim 1, wherein the composition comprises the ligand.

6. The method of claim 1, wherein said cell is a human cell.

7. The method of claim 2, wherein said cell is a human cell.

8. The method of claim 3, wherein said cell is a human cell.

9. The method of claim 4, wherein said cell is a human cell.

10. The method of claim 5, wherein said cell is a human cell.

* * * * *